United States Patent [19]

Koch et al.

[11] Patent Number: 4,982,616

[45] Date of Patent: Jan. 8, 1991

[54] SAMPLING DEVICE FOR INSPECTION VEHICLES

[75] Inventors: Dieter Koch, Weyhe-Leeste; Hans-Jakob Baum, Achim-Uesen, both of Fed. Rep. of Germany

[73] Assignee: Bruker Franzen Analytik GmbH, Fed. Rep. of Germany

[21] Appl. No.: 421,260

[22] Filed: Oct. 13, 1989

[30] Foreign Application Priority Data

Oct. 15, 1988 [DE] Fed. Rep. of Germany ....... 3835207

[51] Int. Cl.$^5$ .............................................. G01N 1/00
[52] U.S. Cl. .................................. 73/864.81; 73/864.71
[58] Field of Search ........... 73/863.31, 863.33, 864.31, 73/864.41, 864.71, 864.81

[56] References Cited

U.S. PATENT DOCUMENTS 3,066,342 12/1962 Jackson et al. .................... 73/864.71

Primary Examiner—Robert Raevis
Attorney, Agent, or Firm—Cohn, Powell & Hind

[57] ABSTRACT

A sampling device for inspection vehicles equipped with an environmental inspection system, the system comprising an analyzer having a receiving head (21), to which the substances to be examined are supplied by means of a movable collecting body (4) having a ground-engageable contact surface. The collecting body is formed by a rope-like material (4) which is wound up on a supply drum (2) and passed between two rollers (10, 11) arranged at a certain distance therefrom. By displacing the material (4) in its longitudinal direction, the material can be moved into a first position in which an end section (41) of the material hangs down and contacts the ground (42), and a second position in which the end section (41), which had been in contact with the ground (42), is positioned opposite the receiving head (21). Consumed end portions (41) can be cut off by means of a separating device.

10 Claims, 3 Drawing Sheets

FIG. 3.
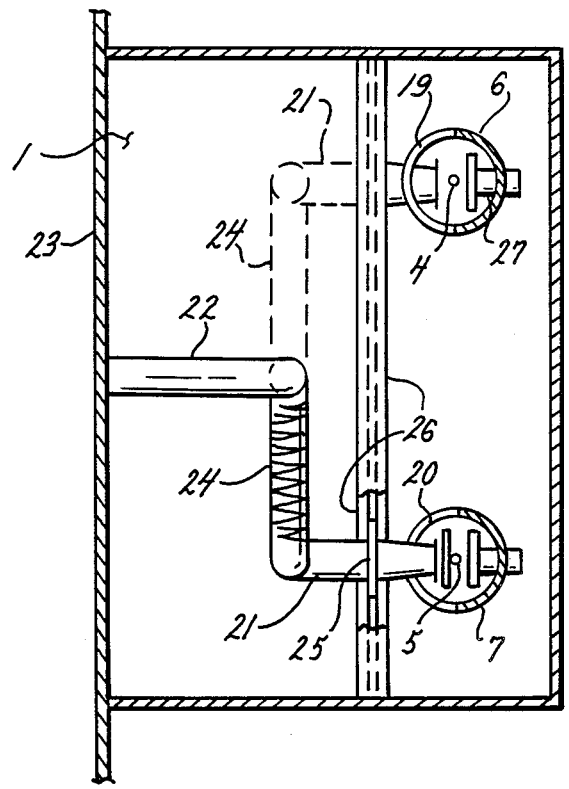
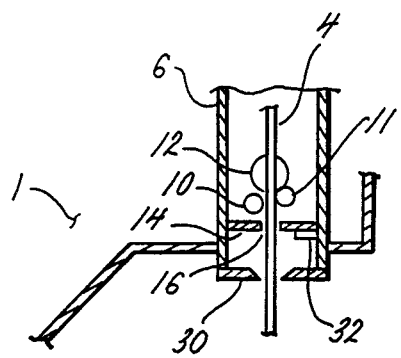
FIG. 4.

SAMPLING DEVICE FOR INSPECTION VEHICLES

The present invention relates to a sampling device for inspection vehicles having a movable collecting body comprising a contact surface, a receiving head of an analyzer, means for lowering and lifting the collecting body by which the contact surface of the collecting body can be moved into contact selectively with the floor carrying the vehicle or the receiving head, and means for exchanging the collecting body.

The principle to collect samples and to transfer them to the receiving head of an analyzer by means of a collecting body has been previously known, for example from DE-CS No. 31 37 765. The collecting body is constituted in this case by a disk consisting of silicon caoutchouc and offering good sorption properties at ambient temperature for picking up substances from the surface of those bodies with which it is brought into contact. The substances so picked up may be of interest for the most diverse examinations and tests, for example in environmental analytics, residue and foodstuff analytics, process and quality control, in medical and clinical analytics, toxicology, microbiology, laboratory animal testing, pharmacology, doping control, criminal technology and forensic medicine. The receiving head of the analyzer comprises a heated diaphragm which is flushed at the back by a carrier gas and which, when brought into contact with the collecting disk, causes the substances picked up by the disk to vaporize so that they will penetrate the contact diaphragm of the receiving head and enter the carrier gas of the analyzer flushing the diaphragm. The analyzer may be a gas chromatograph, a mass spectrometer or a GC/MS combination.

The device known from DE-OS No. 31 37 765 is intended for taking samples manually, by bringing the contact surface of the collecting disk successively into contact with the object whose contamination is to be tested and then with the receiving head of the analyzer. This device is, therefore, suited only for stationary use. However, there is a need to examine large areas for possible contaminations, which is possible only by the use of inspection vehicles. Such an inspection vehicle is available, for example, in the form of the armored cross-country vehicle model "Fuchs" described and illustrated by the leaflet FOX NBC 1006/88 E H O published by Thyssen Henschel in D-3500 Kassel. This vehicle is equipped at its rear with arms carrying wheels on their ends, which wheels are provided with silicon caoutchouc tires and can be brought into contact selectively with the ground across which the vehicle is moving or the receiving head of the analyzer mounted at the rear of the vehicle. The vehicle is equipped with two such arms with wheels so that the collecting body formed by one wheel can pick up contaminations from the ground being passed by the vehicle while the substances picked up by the other collecting body are transferred to the receiving head. Before the arm, which had been in contact with the receiving head last, can be lowered again to the ground, the wheel serving as collecting body must be exchanged in order to ensure that the contaminations which will be transferred to the receiving head by the next contact have really been picked up from the ground section passed last. The exchange of the wheels must be effected manually from inside the vehicle, by means of gloves which are sealed against the vehicle wall. The known device, therefore, is not only complex in design, but also difficult to handle, and requires above all constant attendance by operators.

Now, it is the object of the present invention to design a device of the type described above in such a manner that it operates with a high degree of operating safety and largely automatically.

This object is achieved according to the invention by an arrangement wherein the collecting body is formed by a section of a rope-like material, the means for lowering and lifting the collecting body comprises at least two spaced, first and second guiding and feeding means between which the rope-like material is held in substantially stretched condition and which enable the rope-like material to be displaced in longitudinal direction so as to be moved selectively into a first position in which an end section of the material hangs down from the first guiding and feeding means and contacts the ground by its first contact surface, and a second position in which the contact surface of the end portion, which had been in contact with the ground, is positioned opposite the receiving head, and wherein the means for changing the collecting body comprise separating means for cutting off the end portion of the rope-like material used last.

The device according to the invention, therefore, does not make use of wheels carrying on their periphery a collecting body in the form of a tire. Instead, one simply lets an end portion of a rope-like material slide over the ground to pick up any contaminations present. This end portion of the rope-like material can be lowered to the ground simply by feeding a corresponding length of material out of the vehicle, and can be lifted again and moved into the area of the receiving head of the analyzer in the same simple manner, by retracting a corresponding length of the material. Of course, the arrangement of the guiding and feeding means, of the receiving head of the analyzer and the distance over which the rope-like material is to be advanced and retracted, must be selected in a suitable manner to ensure that the end portion of the rope-like material will safely contact the ground and then be transported safely into the area of the receiving head, without contaminating the surroundings of the receiving head or of other sections of the rope-like material which are to be used later for collecting other samples. It is a particular advantage in this connection that the arrangement of two spaced guiding and feeding means enables the rope-like material to be held constantly in stretched condition so that it does not get into contact with other components of the vehicle, and that a fresh collecting body can be made available for every sampling process, by simply cutting off the end portion of the rope-like material used last, which may have become contaminated, without any necessity to carry out difficult manipulations outside the vehicle. Quite to the contrary, the cutting device, just as the guiding and feeding means, can be operated fully automatically so that no operators are required for the operation of the device.

According to a preferred embodiment of the invention, the receiving head is arranged in the area between the two guiding and feeding means. The rope-like material runs along a defined path in this area, and accordingly it also occupies a defined position relative to the receiving head so that perfect transfer of the substances picked up to the receiving head is ensured. This transfer may even be improved if a pressure element adapted for being moved transversely to the longitudinal direction of the rope-like material is provided opposite the receiving head and the rope-like material is passed between the receiving head and the pressure element. It is then possible, without any difficulty, to establish intimate contact between the rope-like material and the receiving head, by operating the pressure element, whereby the substantially complete transfer to the receiving head of the substances that have been picked up by the contact surface of the rope-like collecting body can be ensured.

According to one preferred embodiment of the invention, the first guiding and feeding means consists of two rollers including the rope-like material between them, with at least one of the said rollers being driven, while the second guiding and feeding means consists of a supply drum for the rope-like material. The rollers constituting the first guiding and feeding means ensure very precise guiding of the rope-like material and are simultaneously capable of advancing and retracting the rope-like material by exactly defined lengths. The supply drum may be driven in a suitable manner for maintaining the rope-like material in stretched condition. This continuous stretched condition helps ensure a no-contact, defined position of the rope-like material in the area between the two guiding and feeding means, while allowing at the same time for a certain lateral deflection of the material, if it should be desired to have the pressure element press the material against the receiving head arranged laterally of the path of the rope.

The risk that any contaminations picked up by the rope-like material may be transferred to the first guiding and feeding means, i.e. in particular to the rollers, which may later lead to incorrect measurements, is extraordinarily insignificant, in particular when the first guiding and feeding means is made from steel, because the affinity of steel relative to the substances adsorbed by the rope-like collecting body is negligible. If in spite of this fact a certain degree of adulteration of the measurements has to be feared, there is always the possibility to pass a section of the fresh rope-like material through the first guiding and feeding means so that any contaminations adhering thereto will be picked up by it, and to cut this section off before another fresh section is lowered to the ground.

The position of the first and second guiding and feeding means relative to each other may, generally, be selected at desire, as in order to establish the contact between the rope-like material and the ground it is only necessary to let the rope-like material hang down from the first guiding and feeding means by gravity. For space-saving reasons, however, it will often be required to arrange the first and second guiding and feeding means vertically above each other.

In order to protect the surroundings of the receiving head of the analyzer from uncontrolled contamination, it is regarded as particularly advantageous if the components of the device according to the invention are accommodated in a pressurized housing comprising a bottom plate with an outlet opening for the rope-like material. The first guiding and feeding means are then conveniently arranged beside this outlet opening in such a manner that the outlet opening is largely closed by them so that the loss of gas escaping through this opening from the pressurized housing is kept relatively small. The use of two parallel rollers as first guiding and feeding means proves to be particular advantageous in this respect, too.

Whereas in the case of the device described at the outset, it is rather difficult to guide arms, which are arranged laterally of the receiving head, in such a manner that the wheels mounted on the arms can be brought into contact with the face of the receiving head with the required accuracy, it is very easy in the case of the device according to the invention to bring two different collecting bodies alternately into engagement with the receiving head. It is only necessary for this purpose to provide the device with at least two arrangements comprising the rope-like material and the relevant guiding and feeding means, and to support the receiving head in such a manner that it can be directed selectively toward the one and the other of the two rope-like materials. When the rope-like material is guided along a straight path, as described before, and arranged for being applied against the receiving head by a pressure element, then the receiving head only has to be pivoted between two defined angular positions, about an axis extending in parallel to two guided material ropes, in order to adjust it exactly and alternately to one or the other rope. However, it would of course also be possible to provide for parallel displacement of the receiving head if it should be regarded as important that the receiving head should always occupy the same angular position relative to the two ropes. This may be important, for example, if a rope-like material of rectangular cross-section, i.e. a tape, is employed. Preferably, however, the rope-like material takes the form of a hose, a hose being uncritical as regards its cross-sectional alignment, while providing on the other hand high flexibility combined with a certain rigidity and strength. Moreover, a hose is particularly well suited for establishing good ground contact even under rough ground conditions, because it is insensitive to damage and because it can be flattened during guiding and feeding and also for the purpose of applying it upon the receiving head so that defined conditions can be achieved here in any case.

The invention will now be described and explained in more detail by way of one embodiment illustrated in the drawing. The features that can be derived from the description and the drawing may be used in other embodiment of the invention individually or in any combination thereof. In the drawings:

FIG. 3 shows a section through the arrangement of FIG. 1, taken along line III/III, and FIG. 4 shows a section through the arrangement of FIG. 2, taken along line IV/IV of FIG. 2.

Figure 1:
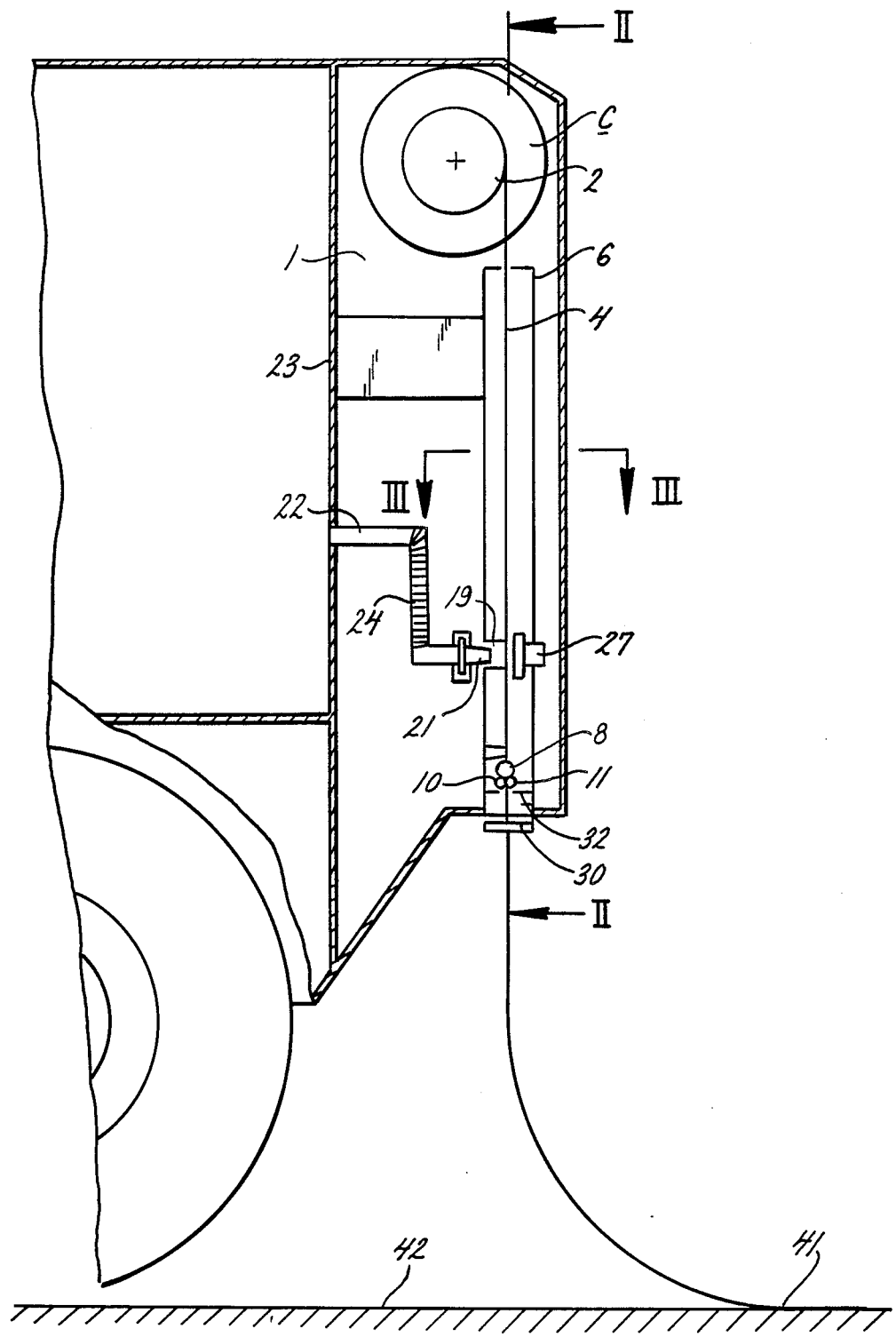
FIG. 1 shows a diagrammatic longitudinal section through the rear portion of an inspection vehicle with a sampling device according to the invention.
Figure 2:
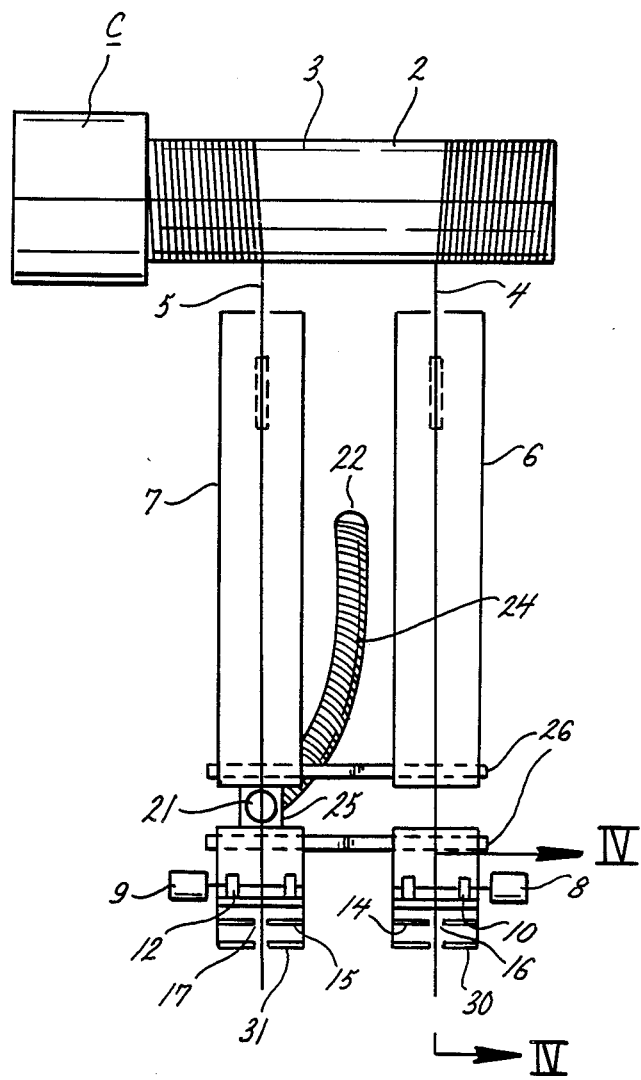
FIG. 2 shows a section through the arrangement of FIG. 1, taken along line II/II.

Regarding the embodiment illustrated in the drawing, the rear end of an inspection vehicle is provided with a compartment 1 comprising in its upper portion two drums 2 and 3 supported on a horizontal shaft and coupled with a common drive unit C. Each of the drums 2 and 3 carries a supply of hose material 4, 5 consisting of a flexible element of silicon rubber or coated with silicon rubber. The free end of each hose extends vertically downward through a surrounding bracket-supported pipe 6 or 7, respectively, to a pair of rollers 10, 11 and drive roller 12 provided with a drive 8, 9. The hose 4, 5 passes these rollers 10, 11 and roller 12 in the manner illustrated in FIG. 4. The pair of rollers 10 and 11 are arranged immediately above a bottom plate 14, 15 closing the pipe 6, 7 and provided with a passage opening 16, 17 for the hose 4, 5. The pairs of rollers are arranged closely adjacent the openings in the bottom plates 14, 15 so that narrow gaps are left only permitting only an insignificant airflow to pass. This enables the housing, which is formed by the compartment 1 and sealed in gas-tight relationship from the interior of the vehicle, to be pressurized so as to prevent any contaminated air from penetrating into the compartment and from interfering with the operation of the components of the device arranged inside the compartment 1.

The housing further accommodates the receiving head 21 of an analyzer which is arranged inside the control vehicle in a manner not shown in detail and connected to the receiving head 21 via a line 22 which is passed in sealed relationship through the wall 23 separating the compartment 1 from the interior of the vehicle. The line 22 comprises a flexible section 24 permitting the receiving head 21 to move. The receiving head 21 is attached to a slide 25 which is guided in two horizontal rails 26 arranged closely above the pairs of rollers 10, 11 and 12. The slide 25, being guided in the rails 26, makes it possible to move the receiving head 21 alternately into positions, in gaps 19, 20, facing the one or the other of the two hoses 4, 5. A pressure element 27 arranged on the side of each hose opposite the receiving head 21 can be moved toward the oppositely arranged receiving head 21, thereby providing the possibility to press the respective hose upon the neighboring receiving head 21.

At a certain distance below the respective bottom plate 14, 15 there are arranged separating devices 30, 31 serving for cutting off the hose portion hanging down from the compartment 1. The separating devices 30, 31 also serve to close the pipe 6, 7 additionally at the bottom and to protect the device in this manner from gross contamination that may be whirled up by the vehicle. The dirt settling on the separating device may be removed in part by the movement of the cutting plates, or else can be washed off by means of a high-pressure cleaning nozzle 32 arranged immediately adjacent the separating device 30 or 31, as illustrated in FIG. 1 for the associated separating device 30.

During operation, the two supply drums 2, 3 are imparted by the drive unit C a given torque in the winding-up direction of the hoses 4, 5 whereas the pairs of rollers 10, 11 and 12, between which the hose 4 or 5 is firmly clamped, serve for either moving the hose 4 or 5 in the axial direction or retaining it in a desired position. The torque exerted by the supply drums 2, 3 has the effect that the hoses 4 and 5 are maintained in stretched condition, at a given stress, within the tubes 6, 7 surrounding them at a certain distance.

It is therefore possible, with the aid of the drives 8 and 9 connected with the pairs of rollers 10, 11 and 12, to advance a section 41 of the respective hose until it slides on the ground 42 passed by the vehicle, as illustrated in FIG. 1. The section 41 of the hose is, therefore, permitted to adsorb any contaminations that may be present on the ground. After a given travelling length, the hose 4 may again be retracted, by corresponding operation of the drive of the pair of rollers 10, 11, until the section 41 of the hose 4, which served as collecting body, has reached the area of the receiving head 21. The distance between the receiving head 21 and the supply drum 2 is large enough to ensure that a contaminated section of the hose will not get into contact with the drum. The circumstance that the contaminated section 41 of the hose passes the pair of rollers 10, 11 is of minor importance because these rollers are made from a material, in particular from steel, which does not pick up any of the substances that have been absorbed by the hose section 41. Once the end portion 41 of the hose 4 then occupies a position in front of the test head 21, this hose section may be pressed upon the receiving head 21, by operation of the pressure element 27, whereupon the receiving head 21 will cause the substances adhering to the hose 4 to be desorbed and transferred to the analyzer. The receiving head may, preferably, consist of a head with heated, timed diaphragm flushed with a carrier gas, of the type used for sampling purposes in gas chromatographs, mass spectrometers or combinations of such devices, and the analyzer installed in the vehicle may be a gas chromatograph, a mass spectrometer or a GC/MS system.

Simultaneously with the retraction of the one hose 4, the other hose 5 is advanced so that uninterrupted sampling is ensured. If the travelling speed is kept constant, the intervals of such operation correspond to defined travelling lengths so that accurate mapping is rendered possible when examining larger area. If after transfer of the substances the receiving head 21 or the respective hose is advanced again, the section 21 of the hose which has been used before is cut off by means of the separating device, once it has left the respective pipe through the opening in its bottom plate. It is ensured in this manner that only fresh hose sections come to slide along the ground whereby any risk of faulty measurements is excluded. If there is a risk that the substances under examination may have been transferred to the coacting pair of rollers, there is always the possibility to advance the hose until the rollers are passed by a clean hose section which removes any residues that may have got stuck to the rollers, whereafter it is cut off together with the consumed hose section.

From the above it appears that the use of a rope-like material, such as the described hose, provides the possibility to scan the surface of the ground for the presence of interesting substances, and to analyze these substances, without any manual operations. In this connection, automatic recording instruments may serve for mapping out contaminated and uncontaminated areas of the ground.

It is understood that the invention is not limited to the illustrated embodiment, but that it can be varied in different ways without leaving the scope and intent of the present invention. This applies for the special design of the feeding means constituted by the supply drums and the pairs of rollers, for the special arrangement and support of the receiving head, the design and arrangement of the separating means, the arrangement of cleaning nozzles, and so on. Further, it would also be possible, for example, to implement the invention with the feeding means arranged horizontally beside each other, instead of vertically above each other.

We claim:

1. In a sampling device for inspection vehicles having a movable collecting body comprising a contact surface, a receiving head of an analyzer, means for lowering and lifting the collecting body by which the contact surface of the collecting body can be moved into contact selectively with the ground carrying the vehicle and the receiving head, and means for replacing the collecting body, the improvement comprising: the said collecting body is formed by a material having a rope-like configuration (4) having an end section (41) providing a contact surface, the said means for lowering and lifting the said collecting body comprises at least two spaced, first and second guiding and feeding means (10, 11; 2) between which the said rope-like configured material (4) is held in substantially stretched condition and which enable the rope-like configured material to be displaced in longitudinal direction so as to be moved selectively into a first position in which said end section (41) of the material hangs down from the said first guiding and feeding means (10, 11) and contacts the ground (42) by said contact surface, and a second position in which the contact surface of the end section, which had been in contact with the ground, is positioned opposite the said receiving head (21), and that the said means for changing the said collecting body comprise separating means (30) for cutting off the end portion (41) of the rope-like configured material (4) used last.

2. Device according to claim 1, in which the said receiving head (21) is arranged in the area between the two guiding and feeding means (10, 11; 2).

3. Device according to claim 1 or 2, in which a pressure element (27) adapted for being moved transversely to the longitudinal direction of the said rope-like material (4) is provided opposite the said receiving head (21) and the rope-like configured material (4) is passed between the said receiving head (21) and the said pressure element (27).

4. Device according to claim 1, in which the said first guiding and feeding means comprises two rollers (10, 11) receiving the said rope-like configured material (4) between them, with at least one of the said rollers being drive, while the second guiding and feeding means consists of a supply drum (2) for the rope-like configured material (4).

5. Device according to claim 4, in which the said supply drum (2) is driven in a suitable manner for maintaining the said rope-like configured material (4) in stretched condition.

6. Device according to claim 1, in which at least the said first guiding and feeding means (10, 11) is made from steel.

7. Device according to claim 1, in which the said first and second guiding and feeding means (10, 11; 2) are arranged substantially vertically above each other.

8. Device according to claim 1, in which a pressurized housing (1) is provided comprising a bottom plate (14) with an outlet opening (16) for the said rope-like configured material (4) and with said first guiding and feeding means (10, 11) arranged immediately beside the said outlet opening (16).

9. Device according to claim 1, in which the device is equipped with at least two arrangements comprising rope-like configured material (4, 5) and associated guiding and feeding means, and said receiving head (21) is supported in such a manner that it can be directed selectively toward the one and the other of the said two rope-like configured materials (4, 5).

10. Device according to claim 1, in which the said rope-like configured material (4) is a hose.

* * * * *

UNITED STATES PATENT AND TRADEMARK OFFICE
CERTIFICATE OF CORRECTION

PATENT NO. : 4,982,616

DATED : January 8, 1991

INVENTOR(S) : Dieter Koch and Hans-Jakob Baum

It is certified that error appears in the above-identified patent and that said Letters Patent is hereby corrected as shown below:

Column 1, line 16, delete "DE-CS", insert "DE-OS".

Column 8, line 1, delete "drive", insert "driven".

Signed and Sealed this

Twenty-first Day of April, 1992

Attest:

HARRY F. MANBECK, JR.

*Attesting Officer*       *Commissioner of Patents and Trademarks*